United States Patent [19]

Hirohara et al.

[11] Patent Number: 4,465,772

[45] Date of Patent: Aug. 14, 1984

[54] METHOD FOR DISINFECTING AND WASHING OF IMMOBILIZED LACTASE

[75] Inventors: Hideo Hirohara, Ibaraki; Hidefumi Yamamoto, Takatsuki; Emiko Kawano, Osaka; Mamoru Hattori, Hekinan; Hisao Yamaguchi, Anjo, all of Japan

[73] Assignee: Sumitomo Chemical Company, Limited, Osaka, Japan

[21] Appl. No.: 307,578

[22] Filed: Oct. 1, 1981

[30] Foreign Application Priority Data

Oct. 6, 1980 [JP] Japan ................................ 55-140176

[51] Int. Cl.³ ...................... C12P 19/02; C12N 11/08; C12N 9/38; A23C 21/02
[52] U.S. Cl. ....................................... 435/105; 426/41; 426/42; 435/180; 435/207; 435/260; 435/800
[58] Field of Search .................... 426/42, 41; 435/174, 435/176, 177, 180, 105, 207, 260, 800; 127/31, 36

[56] References Cited

U.S. PATENT DOCUMENTS 4,239,854  12/1980  Hirohara et al. ................ 435/180 X

FOREIGN PATENT DOCUMENTS 26672     4/1981   European Pat. Off. .
37667    10/1981   European Pat. Off. .
1557944  12/1979   United Kingdom .

OTHER PUBLICATIONS

Olson et al., Immobilized Enzymes in Food and Microbial Processes, Plenum Press, NY, 1974, (pp. 56–61).
Weetall et al., Preparation of Immobilized Lactase, Biotech. & Bioeng., vol. XVI, 1974, (pp. 689–696).
Pitcher, Jr. et al., The Preparation, Characterization and Scale-up of a Lactase System Immobilized to Inorganic Supports for the Hydrolysis of Acid Whey, Methods in Enzymology, vol. XLIV, Academic Press, NY, 1976, (pp. 792–809).
Pitcher, Jr. et al., Development of an Adsorbed Lactase Immobilized Enzyme System, Enzyme Engineering, vol. 3, Plenum Publishing Corp., 1978, (pp. 483–496).
Charles et al., Enzymes Immobilized on Alumina and Stainless Steel Supports, Biotech & Bioeng., vol. XVII, 1975, (pp. 203–210).
Jour. of Food Sci., vol. 42, No. 2, (1975), pp. 291–296.
Chem. Absts., vol. 90, No. 9, (Feb. 26, 1979), p. 389, Abstract 70574x.

*Primary Examiner*—David M. Naff
*Attorney, Agent, or Firm*—Cushman, Darby & Cushman

[57] ABSTRACT

Effective disinfection and washing of immobilized lactase from *Aspergillus oryzae* is carried out after a period of hydrolyzing lactose by treatment of the immobilized lactase with aqueous solutions of pH's 2 to 4 and 6 to 8.7, one or both of which contain a disinfectant. The solution having a pH of 6 to 8.7 may be a phosphate buffered solution. The lactase may be immobilized on a high polymer compound by covalent linkage. The immobilized lactase has outstanding resistance to chemicals and wide pH stability so that decrease of lactase activity is minimized.

23 Claims, No Drawings

METHOD FOR DISINFECTING AND WASHING OF IMMOBILIZED LACTASE

The present invention relates to a method for the disinfection and washing of immobilized lactase. More particularly, the invention pertains to a method wherein the hydrolysis of lactose is effected in a solution containing lactose using an immobilized lactase prepared by the immobilization of the lactase derived from *Aspergillus oryzae*, and then said immobilized lactase is effectively disinfected and washed without losing any enzyme activity.

In a method wherein, after carrying out the hydrolysis reaction of lactose in a solution containing lactose using an immobilized lactase prepared by the immobilization of the lactase derived from *Aspergillus oryzae* on a carrier or an entrapping and flocculating material by the covalent linkage or on a macroporous ion-exchange resin carrier by the adsorption, said immobilized lactase is disinfected and washed, the present invention relates to a method for the disinfection and washing of immobilized lactase which comprises (a) disinfection with a disinfectant aqueous solution of pH2–pH8.7 and washing with an acidic aqueous solution of pH2–pH4 and with an aqueous solution of pH6–pH8.7;

(b) disinfection and washing with a disinfectant aqueous solution of pH2–pH4 and washing with an aqueous solution of pH6–pH8.7;

(c) washing with an aqueous solution of pH2–pH4 and disinfection and washing with a disinfectant aqueous solution of pH6–pH8.7; or (d) disinfection and washing with a disinfectant aqueous solution of pH2–pH4 and disinfection and washing with a disinfectant aqueous solution of pH6–pH8.7.

A solution containing lactose used as a substrate of the reaction by the immobilized lactase is usually milk, whey or the like, which contains proteins and salts and has a tendency to easily cause putrefaction and attachment of curdy or milky substance to the immobilized lactase. Consequently, the disinfection and washing of said immobilized lactase is so important in order to reuse the immobilized lactase that the industrial utilization of the immobilized lactase can not be realized without any effective method for the disinfection and washing.

The present inventors eagerly studied an effective method for the disinfection and washing of an immobilized lactase when the same is repeatedly or continuously used for the hydrolysis of lactose in milk, whey or the like and have succeeded in the completion of the present invention.

As to the disinfection methods, there are one relying on heat and another relying on chemicals or disinfectant; in the case of the former, the immobilized enzyme loses the activity in a temperature range wherein satisfactory disinfection is carried out, resulting in no practical use. Accordingly, the effect of disinfectants and the chemical resistance of the immobilized lactase were studied. As a result, it was found that the special immobilized lactase of the present invention prepared by the immobilization of the lactase derived from *Aspergillus oryzae* is different from the immobilized lactase derived from yeasts or from bacteria and, has an outstanding chemical resistance to a disinfectant aqueous solution and a wide pH stability. Also it was found relating to washing that, owing to the attachment of substances such as proteins to the immobilized lactase during the hydrolysis of lactose in milk, whey or the like, the immobilized lactase appears to show a decrease in its activity and tends to easily cause putrefaction; however, said attached substances can be washed out effectively according to the method for the disinfection and washing specified by said (a)–(d) in the present invention. The fundamental method to wash out the attached substances is washing with water. However, it is extremely difficult to remove the attached substances by only washing with water and it requires a large amount of water resulting in poor efficiency. Thus, it can not be said that the method is a realizable one. For the purpose of washing out the attached substances without the decrease of the enzyme activity, utilization of the outstanding chemical resistance and the wide pH resistance of the immobilized lactase specified by the present invention is ultimately most appropriate. Thus the combination method of the disinfection and washing specified by the present invention was found out.

The mode of the present invention will be described hereinbelow.

As the mode of the lactase immobilized by the covalent linkage in the present invention, there can be illustrated an immobilized lactase generally prepared by the immobilization of the lactase on a carrier or an entrapping and flocculating material by covalent linkage. As a desirable mode, there can be illustrated an immobilized lactase prepared by immobilizing the lactase derived from *Aspergillus oryzae* on a insoluble high polymer compound of a carrier or an entrapping and flocculating material (I) which has at least amino groups and/or substituted amino groups and, in addition, may have carboxyl groups, or (II) which has only hydroxyl groups as functional groups, by the formation of covalent bond between said lactase and said high polymer compound using a covalent bond-forming agent or a multifunctional cross-linking agent. More preferably, there can be illustrated an immobilized lactase which is immobilized by the covalent linkage on a carrier of a macroporous ion-exchange resin selected from the group of (I) a macroporous phenol-formaldehyde type amphoteric ion-exchange resin having at least amino groups and/or substituted amino groups and carboxymethyl groups and (II) a macroporous phenol-formaldehyde type weak basic anion-exchange resin having amino groups and/or substituted amino groups as the ion-exchange groups. More specifically there can preferably be illustrated an immobilized lactase (EPC patent publication No. 26672, published on Apr. 8, 1981) prepared by adsorbing the lactase derived from *Aspergillus oryzae* on a carrier which is a macroporous phenol-formaldehyde type amphoteric ion-exchange resin [particle size: 250–1410μ (preferably 250–840μ)] having polyethylenepolyamine groups and carboxymethyl groups as ion-exchange groups and then immobilizing said lactase on said carrier by covalent linkage owing to the glutaraldehyde treatment.

As the carrier or the entrapping and flocculating material used for the immobilized lactase in the present invention, besides those mentioned above, there can be used any carriers or materials already known as carriers or entrapping and flocculating materials for immobilized enzymes. There is no special limitation on them as far as they are appropriate to achieve the purpose of the present invention. Accordingly, as the substituted amino group mentioned above, conventionally known ones, for instance, diethylaminoethyl (DEAE) and polyethylenepolyamine $-(CH_2CH_2NH)_n$- are illustrated as examples.

Any method known for preparing an immobilized enzyme can be used to immobilize a enzyme on a carrier by covalent linkage.

The immobilized lactase prepared by immobilizing the lactase derived from *Aspergillus oryzae* on an insoluble high polymer compound according to the method mentioned above has outstanding resistance to chemicals and wide pH stability. As to the method for immobilizing the lactase derived from *Aspergillus oryzae* on a carrier by covalent linkage, there is no particular limitation as far as the lactase does not lose the activity. However, the most preferable method is that the lactase is immobilized to the high polymer compound of the carrier or the entrapping and flocculating material forming covalent bond by means of a covalent bond-forming agent or a multifunctional cross-linking agent which reacts with amino groups, hydroxyl groups or guanyl groups in the enzyme.

In the case of the immobilized lactase prepared by adsorption, when the lactase is firmly adsorbed, it has high resistances to chemicals and wide pH stability. As a carrier having a high affinity with the lactase derived from *Aspergillus oryzae*, there can be at first illustrated a macroporous phenol-formaldehyde type amphoteric ion-exchange resin having at least amino groups and/or substituted amino groups and carboxymethyl groups as the ion-exchange groups (U.S. Pat. No. 4,239,854). Also a macroporous phenol-formaldehyde type weak basic anion-exchange resin having at least amino groups and/or substituted amino groups as the ion-exchange groups can be illustrated as a carrier having a high affinity with the lactase derived from *Aspergillus oryzae*.

Preparation and some of the properties of the lactase derived from *Asperlillus oryzae* a few of which are commercially available are already known (for instance; J. Biochemistry, 77, 241–247(1975); J. Biochemistry, 80, 1195–1200 (1976)).

In the present invention, the immobilized lactase thus prepared is disinfected and washed by any means selected from (a)–(d) specified herein and the mode thereof will be described hereinbelow.

At first, as a disinfectant aqueous solution, any aqueous solution which contains a disinfectant compound (hereinbelow referred to as "disinfectant") may be used. For example, as disinfectants, there can be illustrated organic acids such as lactic acid, acetic acid, peracetic acid, propionic acid, malic acid, dehydroacetic acid, citric acid, fumaric acid, tartaric acid, gluconic acid, succinic acid, glutaric acid, adipic acid, salicylic acid and glycine; organic acid esters such as monoglycerides of lower fatty acid; salt of organic acid such as potassium sorbate; positive soaps such as benzalkonium chloride, benzethonium chloride and cetylpyridinium chloride; inorganic materials such as sodium chloride, hydrogen peroxide, sodium hypochlorite; lactones such as glucono-δ-lactone and δ-propiolactone; aldehyde such as glutaraldehyde; alcohol such as ethyl alcohol; antibiotics such as chloramphenicol; iodine type disinfectants, for example, "Diazan" ®, and "Isefall" ® (effective iodine content: 16%) manufactured by Ise Chemical Industries Co., Ltd. and sold by Asahi Glass Co., Ltd. and saturated chloroform.

Taking the fact that the field to which the present invention is utilized is food-relating industries into consideration, aqueous solutions of, among those mentioned above, disinfectants described in Official Documents of Food Additives or disinfectants approved by the Ministry of Health and Welfare in Japan should be usually used.

Disinfectant aqueous solutions mentioned above are used at suitable concentrations for disinfection purpose of each disinfectant.

As to the methods for disinfection and washing, any one of (a)–(d) mentioned below is carried out in the present invention.

(a) disinfection with a disinfectant aqueous solution of pH2–pH8.7 and washing with an acidic aqueous solution of pH2–pH4 and with an aqueous solution of pH6–pH8.7;

(b) disinfection and washing with a disinfectant aqueous solution of pH2–pH4 and washing with an aqueous solution of pH6–pH8.7;

(c) washing with an aqueous solution of pH2–pH4 and disinfection and washing with a disinfectant aqueous solution of pH6–pH8.7; or (d) disinfection and washing with a disinfectant aqueous solution of pH2–pH4 and disinfection and washing with a disinfectant aqueous solution of pH6–pH8.7.

At first, in the case of (a), disinfection is carried out using a disinfectant aqueous solution of pH2–pH8.7. The aqueous solution can be appropriately used either at the pH obtained when the disinfectant is dissolved in water or at the pH obtained by adjusting it with an acid such as hydrochloric acid or an alkali such as sodium hydroxide.

The washing procedure is carried out by washing with an acidic aqueous solution of pH2–pH4 and then with a slightly acidic, neutral or weakly basic aqueous solution of pH6–pH8.7. The order of washing may be reversed. That is, after washing with an aqueous solution of pH6–pH8.7, washing with an aqueous solution of pH2–pH4 may be conducted.

When the disinfection and washing of the present invention is carried out, it is effective to appropriately combine said disinfection and washing.

In the case of (b), there is illustrated a method wherein the washing is carried out with a disinfectant aqueous solution of pH2–pH4 and then an aqueous solution of pH6–pH8.7. Also is effective the method derived by the modification of said method wherein the disinfection is carried out by immersing an immobilized lactase in an acidic aqueous solution of a disinfectant for an appropriate time, the solution is allowed to flow away and then the washing is carried out with an aqueous solution of pH6–pH8.7. This modification of disinfection by immersion is of course applied to not only (b) but also (a), (c) and (d).

(c) is a method wherein, on the contrary to (b), the washing is carried out with an aqueous solution of pH6–pH8.7 containing a disinfectant and then with an acidic aqueous solution of pH2–pH4.

(d) is a method wherein an immobilized lactase is disinfected and washed with an aqueous solution of pH2–pH4 containing a disinfectant and then with an aqueous solution of pH6–pH8.7 containing a disinfectant.

When any method of (a)–(d) mentioned above is carried out, washing with water may be added at need between each of the hydrolysis reaction process and disinfection and washing process. Also the cycles of the disinfection and washing process may be repeated until the purpose is achieved.

There is no particular limitation on the temperature during disinfection as far as it is not higher than 50° C.

Though the temperature is preferebly 20°–30° C., some disinfectants reveal better disinfection effect at around 40° C.

Immobilized lactases other than the specific immobilized lactase of the present invention usually lose the activity when the disinfection and washing procedure described in the present invention is carried out.

The immobilized lactase in the present invention is usually in particle and, in such a case, the reaction is usually carried out in a column. In this case, it is effective to carry out disinfection and washing under packed state of the immobilized lactase without taking out the same from the column. The disinfection and washing can be carried out by either up-flow or down-flow; however, up-flow wherein the procedure is conducted from the bottom to the top of the column is more effective. The advantage of up-flow is that the disinfection and washing can be carried out in a fluidized state of the immobilized lactase in the column by appropriately high flow rate.

According to this up-flow method, the immobilized lactase after the hydrolysis of lactose can be, even if the particles of immobilized lactase are in a mutually aggregated state owing to the attached substances, satisfactorily loosened to each particle, disinfected and washed.

When the flow rate of washing solution is high, high effectiveness can be obtained. However, excessively high flow rate makes immobilized lactase rise up causing washing-away thereof and much consumption of water need.

The SV (space velocity) during washing can be from 1 to about 2000 $hr^{-1}$, preferably 5 to about 500. In order to prevent the immobilized lactase from washing-away, the diameter of the column at the top part is made larger than that at the bottom part so that the linear velocity is decreased at the top part, or a net is attached to the top part of the column. Said disinfection and washing method can be easily carried out automatically by a sequence controller and the like.

In the case of an immobilized lactase prepared by adsorption, the macroporosity of an ion-exchange resin is a necessary property for the stabilization of the enzyme. However, even if the adsorption is conducted tightly, there is shown a tendency to easily cause the liberation of the lactase by repeatedly washing with a solution having a high ionic strength. Accordingly, the ionic strength of washing solution, disinfectant solution or reaction substrate solution is not higher than 0.05, preferably not higher than 0.025. The immobilized lactase prepared by adsorption is usually used for the hydrolysis of lactose in whey permeate with low ionic strength or in pure lactose solution. Also in this case, disinfection and washing is practically important.

The substrate to which the method for the disinfection and washing can be effectively applied is a lactose solution containing proteins. Therefore, various milks and wheys from which proteins are not completely removed fall under the category of said substrate. Of course there is no problem when the method of the present invention is applied to such a substrate as an aqueous solution of lactose or whey from which proteins are completely removed. In the case of a substrate solution which contains a considerably large amount of fat such as whole milk or butter milk, is effective the use of a positive soap such as benzalkonium chloride for the disinfection and washing.

Experiments on Disinfectant Effect and Resistance to Chemicals

Examples of resistance to chemicals shown by the immobilized lactase of the present invention to various disinfectant aqueous solutions are illustrated in Table 1. As the immobilized lactase was used one prepared by using a macroporous phenol-formaldehyde type amphoteric ion-exchange resin (particle size: 250–840µ) as the carrier, making the same adsorb the lactase derived from Aspergillus oryzae and carrying out the glutaraldehyde treatment to cause immobilization by covalent linkage [EPC publication No. 26672 (published on Apr. 8, 1981)].

As shown in Table 1, except 70% ethyl alcohol and 0.01% sodium hypochlorite which caused decrease of activity to some extent, the decrease of activity was within a range of experimental error, that is, any decrease was not seen when said immobilized lactase was immersed in various disinfectant solutions for a long period at 18°–20° C. Also completely no decrease of activity was observed when the immobilized lactase used in the test in Table 1 was immersed in a 1% lactic acid solution, 0.5% "Diazan" solution and 0.5% positive soap solution for five months at room temperature (18°–25° C.). Therefore, these results suggest an effective preservation method for the immobilized lactase of the present invention.

TABLE 1

Disinfectant effect of various chemicals and resistance to chemicals of immobilized lactase

| Chemical | Concentration of chemical | Number of viable cells after 1 hr. | after 7 days | Residual enzyme activity (relative ratio, %) after immersion for 7 days | after immersion for 30 days |
|---|---|---|---|---|---|
| Lactic acid | 1% | ⊖ to ⊕ | ⊖ | 103 | 101 |
| Lactic acid buffer solution | 0.1 M (pH: 3.0) | ⊖ | ⊖ | 98 | 101 |
| Acetic acid | 1% | ⊖ | ⊖ | 102 | 100 |
| Sodium chloride | 10% | ⊖ to ⊕ | ⊖ | 100 | 98 |
| Malic acid | 1% | ⊖ | ⊖ | 101 | 100 |
| Ethyl alcohol | 70% | ⊖ | ⊖ | 84 | 67 |
| Potassium sorbate | 1% | ⊖ | ⊖ | 103 | 101 |
| 35% $H_2O_2$ solution | 1% | ⊖ | ⊖ | 100 | 98 |
| Dehydroacetic acid | 0.1% | ⊖ | ⊖ | 98 | 102 |
| Diazan ® | 0.1% | ⊕ | ⊖ | 101 | 100 |
| (effective iodine content: 1.75%) | 1.0% | ⊖ | ⊖ | 102 | 99 |
| Isefall ® | 0.01% | ⊖ to ⊕ | ⊖ | 96 | 103 |
| (effective iodine | 0.1% | ⊖ | ⊖ | 98 | 98 |

TABLE 1-continued

Disinfectant effect of various chemicals and resistance to chemicals of immobilized lactase

| Chemical | Concentration of chemical | Number of viable cells after 1 hr. | Number of viable cells after 7 days | Residual enzyme activity (relative ratio, %) after immersion for 7 days | Residual enzyme activity (relative ratio, %) after immersion for 30 days |
|---|---|---|---|---|---|
| content: 16%) | | | | | |
| Positive soap (10% benzalkonium chloride) | 0.2% | ⊖ | ⊖ | 97 | 102 |
| | 5.0% | ⊖ | ⊖ | 98 | 101 |
| Sodium hypochlorite (effective chlorine content: not less than 5%) | 0.01% | ⊖ | ⊖ | 96 | 92 |
| Glutaraldehyde | 1.0% | ⊖ | ⊖ | 102 | 98 |
| Control (water) | | ⊕5 | | 102 | — |

The methods and conditions of experiments are as mentioned below.

(1) Disinfecting power (number of viable cells)

Milk obtained commercially was putrefied. Mixture of five strains separated from the putrefied milk was suspended in a 0.2 % bouillon solution (pH: 7.0) so that the number of viable cells attains to $10^5$–$10^6$/ml. To this suspension was added an equal amount of an undiluted solution having a concentration of each chemical twice as high as that to be applied. A cotton plug was corked to each container and sampling was carried out after 1 hour and 7 days. The sample was diluted at need and plating on the standard agaragar culture medium was effected to count the number of colonies.

The symbols related to the number of viable cells designate as follows:

⊖ not detected
⊕ about $10^1$/ml
⊕5 $10^5$–$10^6$/ml (2) Residual enzyme activity One mililiter of an immobilized lactase was immersed and allowed to stand in 30 ml of various disinfectant solutions having a concentration to be applied at 18°–20° C. A small amount of said immobilized lactase was taken out as samples after 7 days and 30 days. The sample was sufficiently washed with an excessively large amount of water and a 0.05 M acetate buffer solution at pH 4.5 and then the residual activity was measured. The relative ratio of said residual activity to the activity of the immobilized lactase before immersion in the chemical solutions which is 860 ILU/g-IML was calculated and expressed as percentage.

(3) Method for the measurement of the activity of immobilized lactase

The measurement of the activity of immobilized lactase was carried out throughout the present specification in accordance with the method described below.

In 30 ml of lactose solution having a concentration of 13.3 (W/V) % prepared by dissolving lactose in a 0.05 M acetate buffer solution of pH 4.5 was immersed 0.2–0.25 ml of an immobilized lactase. The reaction was allowed to proceed at 30° C. under reciprocating shaking (more than 100 rpm with an amplitude larger than 3.5 cm) for 15 minutes. Then the amount of glucose produced was determined with a glucose oxidase-peroxidase-dye system. The amount of enzyme which produces 1μ mol of glucose per minute is defined as one unit (1 ILU). The dry weight of an immobilized lactase is determined as mentioned below. That is, after the termination of the reaction, the immobilized lactase was filtered, dried at 50° C. under reduced pressure for 8 hours or more, placed in a desiccator at room temperature (18°–25° C.) for 1.5 hours or more, the weight thereof was then measured and this value is regarded as the dry weight of the immobilized lactase. The activity of an immobilized lactase is represented by the unit per gram of dry weight (1 ILU/g-IML).

The present invention is illustrated in more detail with reference to the following Examples hereinbelow; however, the invention is by no means limited thereto unless exceeding the spirits and scope of the present invention.

EXAMPLE 1

As the carrier there was selected a macroporous phenolformaldehyde type amphoteric ion-exchange resin (particle size: 250–840μ) having polyethylenepolyamine groups and carboxymethyl groups as ion-exchange groups. The lactase derived from *Aspergillus oryzae* was adsorbed on this carrier and the product was subjected to the treatment with an aqueous solution of glutaraldehyde to form the immobilized lactase wherein the lactase is immobilized on the carrier by covalent linkage (activity: 970 ILU/g-IML). Ten mililiters of this immobilized lactase was packed in a column with a jacket. An aqueous solution of skim milk having a concentration of lactose adjusted to 9% (twice the concentration of lactose in usual milk) was allowed to flow down through said column at a column temperature of 50° C. for 17 hours at SV=9 hr$^{-1}$ The conversion of lactose was 80%. After the termination of the column reaction, water was allowed to pass through the column from the bottom with an up-flow for 30 minutes at SV=20 hr$^{-1}$. Then a solution of "Diazan" ® which is an iodine type disinfectant having a concentration of 0.5% of the original liquid concentration (about pH2.8) was allowed to flow through the column for 10 minutes at SV=20 hr$^{-1}$ and the flow was stopped so that the immobilized lactase was immersed and kept in the solution for one hour at room temperature of 22°–23° C. for disinfection. Then sterilized water was allowed to pass through with up-flow for 15 minutes at SV=40 hr$^{-1}$, a 0.05 M phosphate buffer solution (pH7.9) allowed to pass through with up-flow for 20 minutes at SV=40 hr$^{-1}$ to carry out neutralization and washing of the immobilized lactase in the column.

By carrying out said procedure for disinfection and washing, the white substance which attached to the immobilized lactase was removed and could not be seen at all. In addition, a small amount of the immobilized lactase was taken out from the column and ground in a mortar. Viable cells are counted according to the conventional method. No viable cell was detected. After neutralization and washing with the phosphate buffer solution, the washing with sterilized water was continued for 10 minutes ($SV=30$ hr$^{-1}$), and then the solution of the substrate skim milk was again allowed to flow through the column for 17-20 hours. A series of cycles mentioned above were repeated for 30 times (30 days.). The column was quite clean after the disinfection and washing and no white substance attached could be found. Almost no decrease of the activity due to disinfection and washing was observed during this period.

EXAMPLE 2

Nine mililiters of the same immobilized lactase as that used in Example 1 was packed in a column with a jacket having an inside diameter of 13 mm. A solution of reduced whey (whey powder) having a concentration of 7 W/V. % (pH4.4) was allowed to flow through the column with up-flow at 40° C and at $SV=16$ hr$^{-1}$ for the purpose of continuous hydrolysis of lactose in the whey.

After said column operation for about 16 hours, the washing was conducted with up-flow at $SV=100$ hr$^{-1}$ for 30 minutes so that the immobilized lactase in partially aggregated state due to the flow of the whey solution was loosened to some extent. Then a solution of a positive soap (containing 10 % of benzalkonium chloride) having a concentration of 1/100 of the original liquid concentration (adjusted to pH 5.5 with an acetate buffer solution) was introduced into the column at $SV=20$ hr$^{-1}$ for twenty minutes After that, the flow of the liquid was stopped and the content was allowed to stand at room temperature (21° C.) for 1 hour. Then the column was washed with 200 ml of a phosphate buffer solution at pH 7.8 with up-flow at $SV=200$ hr$^{-1}$ Then a solution of lactic acid having a concentration of 0.05 M (pH2.7) was allowed to flow (up-flow, at $SV=50$ hr$^{-1}$ for 1 hour) for neutralization and washing. Further, the residual lactic acid in the column was allowed to flow away completely with sterilized water (up-flow, at $SV=100$ hr$^{-1}$, for 30 minutes). As a result, the proteins which attached to the immobilized lactase completely disappeared, the particles of the immobilized lactase in an aggregated state was loosened and the column was completely cleaned and no viable cell was detected. The procedure comprising continuous reaction, disinfection and washing mentioned above was repeated for 40 days while keeping the conversion at 80%. It was found that the SV had to be decreased from 16 hr$^{-1}$ to 15 hr in order to keep the conversion at 80% for 40 days and the activity was very slightly decreased which is not due to the disinfection and washing.

EXAMPLE 3

In two columns each with a jacket was packed 9.5 ml of the same immobilized lactase as that in Example 1 except that the activity is 820 ILU/g-IML, respectively. A solution of skim milk prepared so that the concentration of lactose was adjusted to 10% was allowed to flow through in one column at $SV=5$ hr$^{-1}$ and in the other column at $SV=10$ hr$^{-1}$. The substrate solution was allowed to flow for 4 hours per day at 55° C.

The reaction due to the flow of solution, disinfection and washing were repeated for 20 days in accordance with the cycle mentioned below. All solutions were allowed to flow with down-flow.

1. Charging the substrate;
   The substrate solution was allowed to flow at $SV=5$ hr$^{-1}$ and $SV=10$ hr$^{-1}$ for 30 minutes to 1 hour. The milk which flowed out was disposed. The temperature was 55° C.
2. Passing-through of the substrate;
   The substrate solution was allowed to pass through at $SV=5$ hr$^{-1}$ and $SV=10$ hr$^{-1}$ for 4 hours. The temperature was 55° C.
3. Washing with water;
   Carried out at $SV=20$ hr$^{-1}$ for 30 minutes at 55° C.
4. Washing with 0.5% lactic acid solution (pH2.7);
   Allowed to flow at $SV=20$ hr$^{-1}$ for 10 minutes at 45°-50° C.
5. Stopping of pump (disinfection);
   The immobilized lactase was immersed in the lactic acid solution and allowed to stand until the next day at 45°-50° C.
6. Washing with water;
   Carried out at $SV=20$ hr$^{-1}$ for 20 minutes at 45°-50° C.
7. Neutralization and washing with a 0.05 M $Na_2HPO_4$ solution (pH8.2, adjusted with HCl);
   Carried out at $SV=20$ hr$^{-1}$ for 10 minutes at 45°-50° C.
8. Washing with water;
   Carried out at $SV=20$ hr$^{-1}$ for 10 minutes at 45°-50° C.

In each case of $SV=5$ hr$^{-1}$ and $SV=10$ hr$^{-1}$, the conversion on the first day was 96% and 80% and that after 10 days was 95% and 75%; however, that after 20 days decreased to 90% and 60%, respectively. Such a decrease of the activity was not due to disinfection and washing but due to high temperatures during reactions. The immobilized lactase in both columns was very clean and no milky substance (white substance) was found after the disinfection and washing for 20 days. No viable cell was counted in the immobilized lactase.

EXAMPLE 4

A macroporous phenol formaldehyde type weak basic anion-exchange resin (particle size: 250-1,000µ) having polyethylenepolyamine groups was selected as a carrier. The lactase derived from *Aspergillus oryzae* was adsorbed on this carrier and the product was subjected to the treatment with an aqueous solution of glutaraldehyde to form the immobilized lactase wherein the lactase is immobilized on the carrier by covalent linkage (activity: 505 ILU/g-IML). This immobilized lactase was packed in a column with a jacket. An aqueous solution of skim milk prepared so that the concentration of lactose was adjusted to 4.5% was allowed to flow down through the column at 43° C. for 5 hours at $SV=4$ hr$^{-1}$. Then the column temperature was lowered to 23° C. and distilled water was allowed to flow up for one hour at $SV=400$ hr$^{-1}$. However, white milky substance still attached to the immobilized lactase to some extent. Thereupon an aqueous solution of a positive soap (0.1% benzalkonium chloride solution) of pH 7.1 adjusted with sodium hydroxide was allowed to pass through the column for 10 minutes at $SV=10$ hr$^{-1}$. Then the pump to send the solution was stopped. The immobilized lactase was immersed in the positive soap solution for 2 hours for the purpose of the disinfection. Then, after washing with water for 10 minutes at $SV=100$ hr$^{-1}$, a 0.05 M lactate buffer solution (pH 3.0) was allowed to pass through for 20 minutes at $SV=20$ hr$^{-1}$. Owing to this procedure, all the white substances which attached to the immobilized lactase was washed away resulting in cleanliness and viable cells are not detected. On the second day and thereafter, the aqueous solution of the substrate skim milk was allowed to pass through for 5 hours and the same procedures as above including the passing through of said aqueous solution of the positive soap at pH 7.1 for 10 minutes at SV=10 hr$^{-1}$ and other operations were repeated. After 25 cycles (25 days) the activity decreased by only several percent.

EXAMPLE 5

Ten mililiters of the same immobilized lactase as that used in Example 4 was packed in a column having a jacket. A solution of whey powder (a solution obtained after the removal of insoluble substances) having a concentration of 7 W/V % was allowed to flow through with up-flow at SV=5 hr$^{-1}$ to carry out the continuous hydrolysis of lactose in whey. The whey powder used herein was one produced in New Zealand and the solution thereof contained crude proteins in a concentration of 6.5 mg/ml after the removal of insoluble substances.

While the column reaction was continued, a high conversion was constantly maintained for 7–10 hours from the start of the reaction. However, the conversion seemed to decrease thereafter rapidly. It was found that this was due to the attachment of curdy substance mainly consisting of proteins in the whey to the immobilized lactase.

After continuation of the column reaction for 17 hours, the immobilized lactase was taken out and transferred into a beaker which contains a 250 fold diluent of the original solution of an iodine type disinfectant "Diazan" ® (pH2.8). After gentle stirring for about 10 minutes, decantation was conducted. Then, the same disinfectant solution was newly added and the content was stirred similarly to the above-mentioned. After this procedure was repeated 3 times, the content was washed with sterilized water under stirring and then decanted. Then, the washing under stirring with a 0.05 M phosphate buffer solution (pH 7.2), was repeated 3 times. After washing twice with sterilized water in the beaker, the immobilized lactase was packed in the column. The immobilized lactase was clean and no curdy substance was found on the immobilized lactase and no viable cell was counted. When the substrate solution was again allowed to pass through under the same conditions as initial ones, it was found that the conversion perfectly recovered up to the original high level. The procedure mentioned above was repeated 15 times. As a result, the immobilized lactase was clean without any attached substance after the disinfection and washing. The decrease of the conversion was in the range of an experimental error; that is, almost no decrease was observed.

EXAMPLE 6

As the carrier was selected "Diaion WA-21" ® (particle size: 297–1190μ) which is a macroporous (highly porous) polystyrene type weak basic anion-exchange resin having polyethylene-polyamine groups as ion-exchange groups. The lactase derived from *Aspergillus oryzae* was adsorbed on this carrier and then subjected to the treatment with an aqueous solution of glutaraldehyde to form an immobilized lactase (activity: 110 ILU/g-IML).

This immobilized lactase was packed in a column having a jacket and milk obtained commercially (lactose content: 4.5 %) was allowed to pass through the column with down-flow at SV=0.8 hr$^{-1}$ for 5 hours while keeping the column temperature at 50° C. The flow of the substrate solution was stopped and the column temperature was lowered down to 20°–24° C. Then the disinfection and washing were carried out in accordance with up-flow in the following order.

1. Water; Allowed to flow at SV=20 hr$^{-1}$ for 20 minutes.
2. 1/100 diluent of "Osuban" (pH: 5.5); (containing 0.1% benzalkonium chloride) Allowed to flow at SV=5 hr$^{-1}$ for 1.5 hours.
3. Water (sterilized water); Allowed to flow at SV=20 hr$^{-1}$ for 20 minutes.
4. 0.03 M phosphate buffer solution (pH7.6); Allowed to flow at SV=10 hr$^{-1}$ for 1.5 hours.
5. Water (sterilized water); Allowed to flow at SV=20 hr$^{-1}$ for 15 minutes.
6. 0.04 M lactate buffer solution (pH2.9); Allowed to flow at SV=10 hr$^{-1}$ for 1.5 hours.
7. Water (sterilized water) Allowed to flow at SV=20 hr$^{-1}$ for 30 minutes.

In the period from the completion of washing with water mentioned in 7 to the next flow of the substrate, the neutralization and washing were, at need, carried out with a 0.03 M phosphate buffer solution (pH7.6) and then sterilized water was allowed to flow at SV=0.8 hr$^{-1}$. Owing to the procedure mentioned above, the immobilized lactase column was washed cleanly and any white substance or creamy substance was not found. No viable cell was detected on the immobilized lactase.

After the cycle comprising the disinfection and washing and to flow of the substrate solution mentioned above was repeated 10 times, the decrease of the activity was found to be only about 9 %. If the white milky substance still attached to the immobilized lactase after washing, the procedure 1–7 may be repeated once more. When, the procedure is repeated, the time required for the flow of solutions may be shortened to about the half of that in the original procedure.

EXAMPLE 7

Albumin and pullulan were blended with the lactase derived from *Aspergillus oryzae* and they were dissolved. Glutaraldehyde was added to this solution. A gel type immobilized lactase was prepared by adding said solution dropwise to a mixed solvent of toluene and chloroform and immobilizing the lactase on an entrapping and flocculating material by covalent linkage (particle size: 0.3–0.8 mm, activity: 185 ILU/ml immobilized lactase). Ten mililiters of this immobilized lactase was added to 100 ml of a whey powder solution (concentration of lactose: 4.8%, pH6.2) in a glass reaction vessel and the content was allowed to react by stirring with a reciprocating shaker at 120 RPM (amplitude: 4 cm) for 5 hours while keeping the temperature at 50° C. Then the whey solution was filtered. The immobilized lactase was placed in a glass reaction vessel and the disinfection and washing were carried out in accordance with the same procedure as that in Example 5 while keeping the temperature at 20°–24° C. Curdy substance which attached to the immobilized lactase was perfectly cleaned out. No viable cell was counted on the immobilized lactase. The procedure comprising the reaction and the disinfection and washing was repeated 18 times. The decrease of the activity was within a range of an experimental error; that is, almost no decrease was observed.

EXAMPLE 8

There is an immobilized lactase prepared by immobilizing the lactase derived from *Aspergillus oryzae* on the same carrier as that in Example 1 by adsorption (activity: 870 ILU/g-IML). Eight mililiters of this immobilized lactase was packed in a column with a jacket and a desalted and deproteinized whey solution was allowed to flow down while keeping the column temperature at 40° C. so that lactose is subjected to a continuous hydrolysis. This whey solution was prepared by carrying out desalting and deproteinization with a cation-exchange resin and an anion-exchange resin so that the specific conductivity $\kappa$ was lowered to 1,000 $\mu\mho$/cm or less which corresponds to ionic strength less than 0.025. The solution had a lactose concentration of 4.5% and the pH 4.5 was adjusted with HCl. After the column reaction for 5 hours, the pump for jacket circulating water was switched off so that the temperature naturally decreased to room temperature of 21°-24° C. The column was washed with water at SV=20 hr$^{-1}$ for 30 minutes. After a 0.1% lactic acid solution (about pH 2.8) was introduced to the column at SV=20 hr$^{-1}$ for 10 minutes, the pump was stopped. After the immobilized lactase was immersed and allowed to stand in the solution until the next day, it was washed with water at SV=20 hr$^{-1}$. Then the neutralization and washing was carried out with a 0.01 M phosphate buffer solution (pH 7.8) for 10 minutes (at SV=20 hr$^{-1}$). After it was further washed with water for 10 minutes at SV=20 hr$^{-1}$, the whey solution was again allowed to flow down under the same conditions as those in the preceding day. This cycle was repeated 20 times (20 days). After 20 days the decrease of activity was within a range of an experimental error; that is, almost no decrease was observed. The immobilized lactase was extremely clean and no viable cell was detected.

1. A method comprising hydrolyzing lactose in a solution with an immobilzed lactase prepared by the immobilization of the lactase derived from *Aspergillus oryzae*, then after a period of use, disinfecting and washing the immobilized lactase by treating the immobilized lactase with an aqueous solution containing a disinfectant and having a pH of 2 to 8.7 and then (a) washing the thus treated immobilized lactase with an acid aqueous solution of pH 2 to 4 and further treating the immobilized lactase with a phosphate buffered aqueous solution of pH 6 to 8.7, or (b) washing the thus treated immobilized lactase with a phosphate buffered aqueous solution of pH 6 to 8.7 and further treating the immobilized lactase with an acid aqueous solution of pH 2 to 4.

2. A method according to claim 1 wherein the immobilized lactase has been prepared by immobilization of the lactase on a carrier by the covalent linkage.

3. A method according to claim 1 including the steps of washing with water after the treatment with the disinfectant containing aqueous solution of pH 2 to 8.7 but before the treatment (a) with the acid aqueous solution of pH 2 to 4 and also in the step (a) washing with water after the treatment with the acid aqueous solution but before the further treatment with phosphate buffered aqueous solution of pH 6 to 8.7 and washing with water after the treatment with the phosphate buffered aqueous solution of pH 6 to 8.7.

4. A method according to claim 1 including the steps of washing with water after the treatment with the disinfectant-containing acid aqueous solution having a pH of 2 to 8.7 but before treatment in (b) with the phosphate buffered aqueous solution of pH 6 to 8.7 and again washing with water after the washing with the phosphate buffered aqueous solution of pH 6 to 8.7 but before treating with the acid aqueous solution having pH 2 to 4.

5. A method according to claim 1 wherein the immobilized lactase has been prepared by immobilization of the lactase by covalent linkage with an insoluble high polymer compound
    (a) which has at least amino groups and/or substituted amino groups or, in addition, has carboxyl groups, or
    (b) which has only hydroxyl groups as functional groups.

6. A method according to claim 5 wherein the carrier on which the lactase is immobilized by covalent linkage is a macroporous ion-exchange resin which is
    (a) a phenol-formaldihyde ion-exchange resin having at least amino groups and/or substituted amino groups and carboxymethyl groups, or
    (b) a phenol-formaldehyde weak basic anion-exchange resin having amino groups and/or substituted amino groups.

7. A method comprising hydrolyzing lactose in a solution with an immobilized lactase prepared by the immobilization of the lactase derived from Aspergillus oryzae, then after a period of use, disinfecting and washing the immobilized lactase by treating the immobilized lactase with an aqueous solution containing a disfectant and having a pH of 2 to 4 and then washing the thus treated immobilized lactase with a phosphate buffered aqueous solution of pH 6 to 8.7.

8. A method according to claim 7 wherein the immobilized lactase has been prepared by immobilization of the lactase on a carrier by the covalent linkage.

9. A method according to claim 7 including the step of washing with water after the treatment with the disinfectant solution but before the treatment with the phosphate buffered aqueous solution of pH 6 to 8.7.

10. A method according to claim 7 wherein the immobilized lactase has been prepared by immobilization of the lactase by covalent linkage with an insoluble high polymer compound
    (a) which has at least amino groups and/or substituted amino groups or, in addition, has carboxyl groups, or
    (b) which has only hydroxyl groups as functional groups.

11. A method according to claim 8 wherein the carrier on which the lactase is immobilized by covalent linkage is a macroporous ion-exchange resin which is
    (a) a phenol-formaldehyde ion-exchange resin having at least amino groups and/or substituted amino groups and carboxymethyl groups, or
    (b) a phenol-formaldehyde weak basic anion-exchange resin having amino groups and/or substituted amino groups as functional groups.

12. A method comprising hydrolyzing lactase in a solution with an immobilized lactase prepared by the immobilization of the lactase derived from *Aspergillus oryzae*, then after a period of use, disinfecting and washing the immobilized lactase by washing the immobilized lactase with a disinfectant-containing aqueous solution having a pH of 6 to 8.7 and then disinfecting and washing the thus treated immobilized lactase with an aqueous solution of pH 2 to 4.

13. A method according to claim 12 wherein the treatment at pH 6 to 8.7 is with a phosphate buffered aqueous solution.

14. A method according to claim 12 including the step of washing with water after the treatment with the disinfectant-containing aqueous solution having a pH of 6 to 8.7 but before the treatment with the aqueous solution having a pH of 2 to 4 and again washing with water after the treatment with the aqueous solution having a pH of 2 to 4.

15. A method according to claim 12 wherein the immobilized lactase has been prepared by immobilization of the lactase on a carrier by the covalent linkage.

16. A method according to claim 12 wherein the immobilized lactase has been prepared by immobilization of the lactase by covalent linkage with an insoluble high polymer compound
    (a) which has at least amino groups and/or substituted amino groups or, in addition, has carboxyl groups, or
    (b) which has only hydroxyl groups as functional groups.

17. A method according to claim 15 wherein the carrier on which the lactase is immobilized by covalent linkage is a macroporous ion-exchange resin which is
    (a) a phenol-formaldehyde ion-exchange resin having at least amino groups and/or substituted amino groups and carboxymethyl groups, or
    (b) a phenol-formaldehyde weak basic anion-exchange resin having amino groups and/or substituted amino groups as functional groups.

18. A method comprising hydrolyzing lactose in a solution with an immobilized lactase prepared by the immobilization of the lactase derived from Aspergillus oryzae, then after a period of use, disinfecting and washing the immobilized lactase by treating the immobilized lactase with an aqueous solution containing a disinfectant and having a pH of 2 to 4 and then disinfecting and washing the thus treated immobilized lactase with a disinfectant-containing aqueous solution of pH 6 to 8.7.

19. A method according to claim 18 wherein the treatment at pH 6 to 8.7 is with a phosphate buffered aqueous solution.

20. A method according to claim 18 including the step of washing with water after the treatment with the disinfectant-containing solution having a pH of 2 to 4 but before the treatment with the disinfectant-containing solution having a pH of 6 to 8.7 and again washing with water after the treatment with the disinfectant-containing solution having a pH of 6 to 8.7.

21. A method according to claim 18 wherein the immobilized lactase has been prepared by immobilization of the lactase on a carrier by the covalent linkage.

22. A method according to claim 21 wherein the immobilized lactase has been prepared by immobilization of the lactase by covalent linkage with an isoluble high polymer compound
    (a) which has at least amino groups and/or substituted amino groups, or in addition, has carboxyl groups, or
    (b) which has only hydroxyl groups as functional groups.

23. A method according to claim 21 wherein the carrier on which the lactase is immobilized by covalent linkage is a macroporous ion-exchange resin which is
    (a) a phenol-formaldehyde ion-exchange resin having at least amino groups and/or substituted amino groups and carboxymethyl groups, or
    (b) a phenol-formaldehyde weak basic anion-exchange resine having amino groups and/or substituted amino groups as functional groups.

* * * * *